United States Patent
Buisan Ferrer et al.

(10) Patent No.: US 11,713,182 B2
(45) Date of Patent: Aug. 1, 2023

(54) DEVICE SUITABLE FOR DISPENSING LIQUID SUBSTANCES

(71) Applicant: BRILL ENGINES, S.L., Barcelona (ES)

(72) Inventors: Josep Buisan Ferrer, Barcelona (ES); Laura Nieto Cavia, Barcelona (ES)

(73) Assignee: BRILL ENGINES, S.L., Barcelona (ES)

( * ) Notice: Subject to any disclaimer, the term of this patent is extended or adjusted under 35 U.S.C. 154(b) by 65 days.

(21) Appl. No.: 17/611,386

(22) PCT Filed: Apr. 22, 2020

(86) PCT No.: PCT/ES2020/070254
§ 371 (c)(1),
(2) Date: Nov. 15, 2021

(87) PCT Pub. No.: WO2020/229713
PCT Pub. Date: Nov. 19, 2020

(65) Prior Publication Data
US 2022/0204251 A1    Jun. 30, 2022

(30) Foreign Application Priority Data
May 16, 2019   (EP) ..................................... 19382382

(51) Int. Cl.
*B65D 83/54*       (2006.01)
*A61F 9/00*        (2006.01)

(52) U.S. Cl.
CPC .......... *B65D 83/546* (2013.01); *A61F 9/0008* (2013.01)

(58) Field of Classification Search
CPC ..... B65D 83/546; B65D 83/752; A61F 9/008; B05B 7/241; B05B 7/2418; B05B 7/2424; B05B 7/2467; B05B 1/12
(Continued)

(56) References Cited

U.S. PATENT DOCUMENTS

| 3,377,004 A | 4/1968 | Kjelson |
| 4,880,161 A | 11/1989 | Wright |

(Continued)

FOREIGN PATENT DOCUMENTS

| EP | 2 127 581 A1 | 12/2009 |
| EP | 2 992 967 A1 | 3/2016 |

OTHER PUBLICATIONS

International Search Report for PCT/ES2020/070254 dated Aug. 5, 2020.

(Continued)

*Primary Examiner* — Vishal Pancholi
(74) *Attorney, Agent, or Firm* — Sughrue Mion, PLLC (57) ABSTRACT

A device suitable for dispensing a liquid substance, such as an ophthalmological substance, including a container; a dispenser for dispensing the substance and which includes a piston element, loaded by the pressure of the pressurized substance so as to adopt a standby position by default that prevents the preloading chamber from being flooded by a dose of the substance; and a valve element capable of enabling a connection between the preloading chamber and the outside. The device has an actuation mechanism that sequentially compresses a volume of air used for moving the piston element from the standby position thereof, allowing a dose of the substance to flood the preloading chamber to subsequently mechanically actuate the valve element and simultaneously enable the connection to the outside of the preloading chamber as well as of the volume of air previously used for moving the piston element from the standby position thereof.

14 Claims, 8 Drawing Sheets

(58) Field of Classification Search
USPC ............................................................ 222/491
See application file for complete search history.

(56) References Cited

U.S. PATENT DOCUMENTS

| | | | |
|---|---|---|---|
| 7,661,561 B2 | 2/2010 | Ophardt et al. | |
| 8,292,131 B2* | 10/2012 | Pruvot | B05B 11/1074 |
| | | | 222/378 |
| 9,072,412 B2* | 7/2015 | Ciavarella | A47K 5/14 |
| 9,266,135 B2* | 2/2016 | Harms | B05B 11/1025 |
| 2004/0084481 A1 | 5/2004 | Foster et al. | |
| 2010/0163582 A1* | 7/2010 | Collins | B05B 11/107 |
| | | | 222/321.6 |
| 2010/0308082 A1* | 12/2010 | Lamble | B05B 11/1074 |
| | | | 222/162 |
| 2013/0284763 A1 | 10/2013 | Banks et al. | |

OTHER PUBLICATIONS

European Search Report for EP 19 38 2382 dated Nov. 11, 2019.
Written Opinion for PCT/ES2020/070254 dated Aug. 5, 2020.

* cited by examiner

DEVICE SUITABLE FOR DISPENSING LIQUID SUBSTANCES

CROSS REFERENCE TO RELATED APPLICATIONS

This application is a National Stage of International Application No. PCT/ES2020/070254 filed Apr. 22, 2020, claiming priority based on European Patent Application No. 19382382.0 filed May 16, 2019.

TECHNICAL FIELD OF THE INVENTION

The invention relates to a device suitable for dispensing liquid substances, and is particularly suitable for dispensing a liquid pharmaceutical substance, such as an ophthalmological substance, contained in a container.

BACKGROUND OF THE INVENTION

Many technical solutions which allow a liquid substance contained in a container to be dispensed are currently known.

Not all known solutions are suitable for dispensing ophthalmological products or products intended to be applied to the human eye. For example, solutions in which the substance to be dispensed is pressurized and contained in a container and mixed with a pressurized gas which acts as a propellant are not suitable.

Among known solutions that are indeed suitable for dispensing an ophthalmological product are those which comprise a dispenser that comprises a suction part for aspirating the liquid substance stored in a container; a pumping part with a piston element coupled to one side of the suction part in order to carry out the pumping operation, such that the substance is discharged or sprayed in a previously determined amount; and an outlet installed on an upper end of the pumping part to release the medicine. One example is described in the patent document EP2992967.

The outlet installed on the upper end of the aforementioned pumping part can be configured in different ways. In EP2992967 two different forms are envisaged, one of them being suitable for dispensing an ophthalmological substance in a drop format and the other being suitable for administering another type of substance in a spray mode, such as for spraying the substance into the nose. In the second form, the dispenser is provided with vortex forming grooves to enable the aforementioned spray mode.

One object of the present invention is a device that offers an alternative to known devices, which does not require suctioning from the container, applying negative pressures, an amount of substance each time one wants to dispense the substance and which is able to always obtain the same amount of substance, hereinafter referred to as dose, outside of the container.

Ophthalmological substances are generally more viscous than water. This fact makes it significantly difficult to reach objectives such as controlling the amount of substance to be released, the outlet pressure, and other objectives.

Among the other objectives there is one that is of special importance: being able to select the way in which the dose of the substance is released.

On the one hand, the solution with vortex forming grooves implemented in the dispenser according to EP2992967, in the variant of administering a substance into the nose, can be suitable for dispensing substances in the spray mode with viscosities that are similar to that of water, but is not suitable for nebulizing ophthalmological products with greater viscosities. A solution such as the one proposed by EP2992967 would require having to significantly increase the outlet pressure of the substance.

On the other hand, in EP2992967 two different variants are envisaged for the dispenser, according to the outlet mode: either drop or spray.

Not only does the form of the outlet vary in these two variants, but the high pressure that would be required to nebulize the substance is not beneficial if one wants to dispense in drop mode. Specifically, the dispenser must be equipped with brake means for the piston of the pumping part, or other means for reducing the outlet pressure of the substance.

A solution that is suitable for being able to nebulize ophthalmological substances is desirable. Furthermore, it is desirable that the same device also be suitable for releasing or dispensing a dose of a viscous substance in the form of a drop and also in a nebulized form, to be decided by the user, all without losing control of the exact amount of dose to be administered.

Therefore, another object of the present invention is a device able to offer this feature in an easy and simple way, which is, as a result, industrially viable. By industrially viable we mean solutions that do not entail an excessive cost for the device, hence excluding it from the market.

Moreover, it is also desirable for the device to be prepared or compatible with solutions that guarantee a constant outlet pressure, regardless of the amount of substance remaining in the container.

DESCRIPTION OF THE INVENTION

The device proposed is a device according to claim 1, suitable for applying a liquid substance, such as an ophthalmological substance, to be applied to the human eye.

The device comprises
 a container that contains the substance to be dispensed at a pressure P greater than atmospheric pressure and
 a dispenser for dispensing the substance to the outside that includes a piston element, loaded by the pressure of the pressurized substance to adopt a standby position by default which prevents a preloading chamber from being flooded by a dose of the substance to be dispensed at a pressure p substantially equal to the pressure P inside the container, and a valve element, capable of enabling a connection between the aforementioned preloading chamber and the outside.

The device further incorporates
 an actuation mechanism of the dispenser that sequentially first compresses a volume of air, the pressure of which is used to move the piston element from the standby position thereof, allowing a dose of the substance to flood the preloading chamber, to subsequently mechanically actuate the valve element and simultaneously enable the connection of the aforementioned preloading chamber to the outside, as well as of the volume of air previously used for moving the piston element from the standby position thereof.

In practice, two currents of fluid to the outside are obtained, one formed by the dose of the substance and the other formed by the volume of previously compressed air and used to move the piston element from the standby position thereof. This offers the possibility of dispensing these currents together or separately, which makes different dispensing modes possible.

In one variant of the invention, the actuation mechanism comprises pumping means capable of pumping and compressing a volume of air captured from the outside, which is used to move the piston element from the standby position thereof, and a trigger prepared to mechanically actuate the valve element.

In this variant, it is envisaged that the actuation mechanism has a movable actuator which in a single stroke of movement first actuates the pumping means causing the movement of the piston element from the standby position thereof, and that a dose of the substance floods the preloading chamber, subsequently actuating the trigger, and with it the valve element to simultaneously enable the connection to the outside of the aforementioned preloading chamber as well as of the volume of air previously used for moving the piston element from the standby position thereof.

According to a desired embodiment, the valve element is prepared to produce an in-line mixture of the dose of the substance and of the volume of air before the ejection thereof to the outside. Moreover, the valve element not only enables a connection to the outside of the dose accumulated in the preloading chamber and of the volume of compressed gas, but can also be adapted to produce an in-line mixture dose of the substance and air.

Furthermore, in a desired embodiment, the volume of the preloading chamber and the volume of pumped air is selected in such a way that the proportion of the dose mass and air mass that are mixed cause an effervescent effect of the ejected substance.

This effervescent effect makes it possible to nebulize said substance without having to use high pressures to impel the substance to be dispensed.

In one embodiment, the dispenser comprises a tubular formation in which the piston element is snugly movable between the standby position, which is normally used due to the effect of the pressure exerted by the pressurized substance in the container on the aforementioned piston element, and a loading position, the piston element being related to one or several fixed parts of the device such that it determines an expansion chamber, expandable, the increase in volume of which, due to the air pumped inside the same, promotes the movement of the piston element towards the loading position, and to another fixed part or parts of the device such that it determines the preloading chamber, floodable with the dose of the substance to be dispensed when the piston element moves to the loading position.

The piston element further comprising a first communication path for air between the expansion chamber and a collector formed in the piston element, a second communication path for the dose of substance between the preloading chamber and the aforementioned collector formed in the piston element, and a third communication path for the substance between the inside of the container and the preloading chamber, all of this with the valve element plugged into the collector of the piston element with a certain degree of play and in such a way that the relative position thereof with respect to the collector enables or disables the fluidic connections between the first and second communication paths to the outside, the valve element being forced to adopt a closed position by default with respect to the piston element, which is the position that disables said fluidic connections to the outside;

the actuator of the actuation mechanism being movable according to a actuation stroke from a standby position to a dispensing position.

All of the foregoing is carried out such that:

in a first movement phase the actuator impels the air captured from the outside towards the expansion chamber, compressing it in the same, increasing the volume thereof and promoting the movement of the piston element to the loading position thereof, creating the necessary space in the preloading chamber so that through the third communication path it is automatically flooded by the dose of substance to be ejected at the pressure p substantially equal to the pressure P inside the container, and in a second movement phase the actuator drags the trigger in motion and with it the valve element, moving it with respect to the collector until the valve element adopts the ejection position which enables the aforementioned fluidic connections between the first and second communication paths of air and the dose of the substance, respectively, to the outside.

In a constructive variant, the valve element is plugged guided into the collector with play in an axial direction, coinciding with the direction of movement of the piston element between the standby and loading positions thereof, the movement in this axial direction being the movement that enables or disables the fluidic connections between the first and second communication paths of air and of the dose of substance, respectively, to the outside.

According to one variant of the invention, the valve element comprises a central ejection tube and a distribution circuit for the dose of the substance which makes it possible in the ejection position to channel the dose supplied to the valve element from different outlets to the central ejection tube through the second communication path of the piston element.

With the aim of producing an in-line mixture of substance and air, the distribution circuit for the dose of the substance can comprise at least two conduits that converge at the central ejection tube.

The valve element can have several air distribution circuits, which will allow the user to select between several dispensing modes to dispense the substance, such as nebulized mode or drop mode.

Thus, in a particularly desirable variant of the invention it is provided that the valve element has a first air distribution circuit which, in an ejection position, makes it possible to channel the air supplied to the valve element to the central ejection tube through the first communication path of the piston element to produce an in-line mixture of substance and air.

It is envisaged that the same valve element has a second air distribution circuit that makes it possible in another ejection position to channel the air supplied to the valve element, through the first communication path of the piston element, to the outside, but outside of the central ejection tube.

To select between the first and second air distribution circuits, it is envisaged that the valve element be able to move, rotating about itself.

Thus, in a constructive variant, the valve element is plugged into the collector, the angular position between the valve element and the piston element being able to vary in order to select the air distribution circuit to connect to the first communication path of the piston element that supplies the air to be ejected and thereby selecting whether or not it produces the mixture of substance and air.

To guarantee a constant pressure P in the container, regardless of the amount of remaining substance, in one variant of the invention the substance is enclosed in the container, subjected to the pressure of a push-piston with an expanded head, to which atmospheric pressure is applied to one side and a vacuum to the other.

With the aim of achieving a pressure P that is sufficient enough to produce, if desirable, the effervescent effect of dose of the substance in a constructive way, the container comprises an outer enclosure with a tubular configuration with at least

- an end portion, with a large transverse cross section, P1, and
- a containment portion, with a small transverse cross section, P2, originally full with the substance and in communication with the dispenser;

And a multiplier piston with

- an expanded head, with a transverse cross section P1' corresponding to that of the end portion of the outer enclosure and which slides with sealed support over the wall of said end portion, and
- a push-piston, with a transverse cross section P2' corresponding to that of the containment portion of the outer enclosure and which slides with sealed support over the wall of said containment portion, the push-piston and the end portion of the enclosure determining an annular chamber under vacuum condition, with a variable volume according to the instantaneous position of the multiplier piston.

The previously mentioned terms large and small are not used with respect to an absolute reference, but are rather simply used to indicate that P1>P2. This means that P1'>P2'.

The P2'/P1' ratio can be close to 1/2, although in this specific case P1' is approximately twice P2'.

BRIEF DESCRIPTION OF THE DRAWINGS

FIGS. 8 to 11 are detailed views of the area corresponding to the play between the piston element and the valve element, the valve element adopting several possible ejection positions, specifically:

DETAILED DESCRIPTION OF THE INVENTION

A device 1 that exemplifies the invention comprises a container 3 that contains a substance to be ophthalmologically applied, typically with a kinetic viscosity between 1 mm$^2$ and 50 mm$^2$/s that is subjected to pressure P conditions greater than the atmospheric pressure. The container 3 is closed at the top by a dispenser 4 with means for enabling a connection between the inside of the container 3 and the outside.

This connection, however, is not direct, the dispenser 4 being configured to only release a single dose of the substance previously accumulated in the preloading chamber to the outside, which intermediates between the inside of the container 3 and the outside.

An actuation mechanism 6 of the dispenser 4, by means of mobile parts, will first allow a dose of the substance to accumulate in said preloading chamber; and then enable a connection between the same and the outside. The actuation mechanism will use a volume of air captured from the outside to actuate some of the mobile parts, the volume of air also being able to be used to produce an in-line mixture of air/substance when the dose of substance is released from the preloading chamber.

Figure 1A:
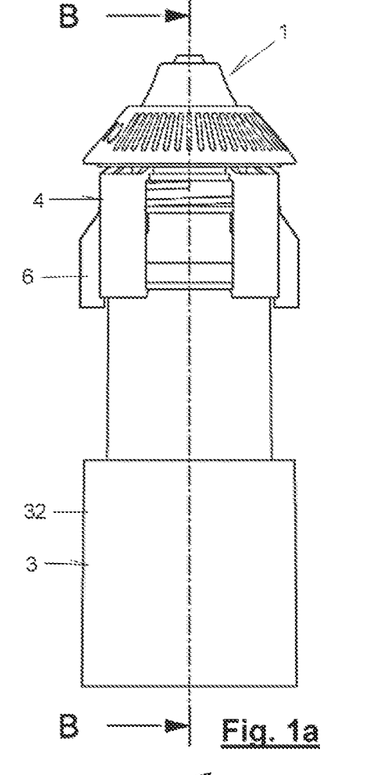
FIG. 1a shows a device that exemplifies the present invention.
Figure 1B:
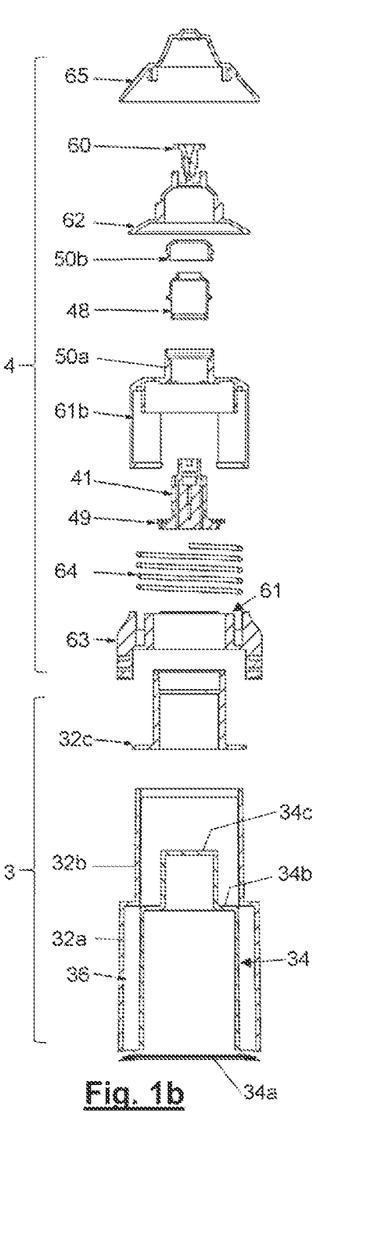
FIG. 1b is an exploded view of the main components of the device of FIG. 1.
Figure 2A:
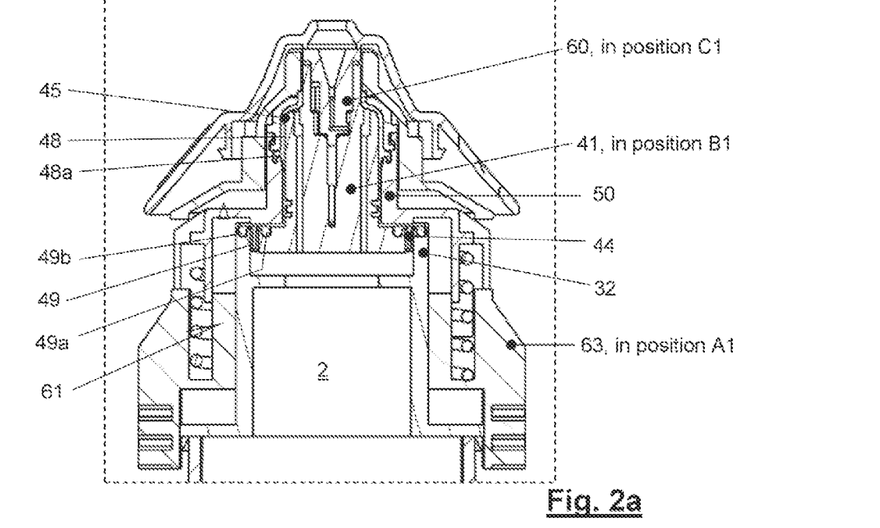
FIGS. 2a and 2b are detailed views of a longitudinal cross section of the device of FIG. 1, specifically of the area corresponding to the dispenser, according to respective cutting planes at 90° to each another, with the piston element adopting a standby position B1 by default and the valve element adopting a closed position C1.
Figure 2B:
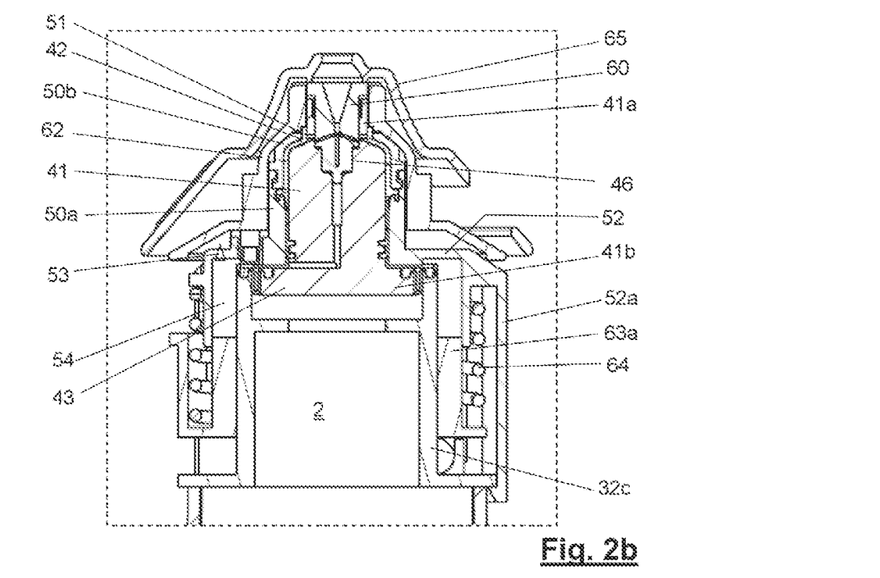

FIGS. 2A and 2b show a detailed view of the dispenser 4 coupled to the opening of the container 3, specifically to a neck 32c said container is provided with. With the help of FIGS. 2A and 2b, along with the exploded view of FIG. 1b, the interrelation between the components of the dispenser 4 and the mechanism 6 that make the aforementioned operation possible is described below.

The mounting position, the dispenser 4 and the container 3 encapsulate a piston element 41. The piston element 41 moves snugly through a fixed tubular formation 50, the piston element protruding through the two opposite ends, upper and lower 41a and 41b, thereof, respectively, of said tubular formation 50.

The tubular formation 50 has an upper narrow passage 51 that cooperates with an outer annular step 42 acting as a transition between two portions of different widths of the piston element 41 to determine between the same a preloading chamber 45, the volume of which will depend on the instantaneous position of the piston element 41 with respect to the tubular formation 50. In the example, this upper narrow passage 51 of the tubular formation 50 is formed by an upper crown 50b, originally a separate piece, coupled to a main portion 50a of the tubular formation 50.

The tubular formation 50, specifically the main portion 50a of the same, has a lower finish with an annular edge 52 that fits over the opening of the neck 32c of the container 3 that cooperates with an expanded base 43 of the piston element 41 and with the aforementioned neck 32c to determine between the same an expansion chamber 44, the volume of which will determine the instantaneous position of the piston element 41. This expansion chamber 44 is intended and is suitable to be filled with a volume of air captured and impelled from the outside of the device 1.

The seal between the tubular formation 50 and the piston element 41 for forming the preloading chamber 45 is ensured in the example by means of a first elastic membrane 48 in the form of a collar, the upper end of which is trapped between the upper crown 50b of the tubular formation 50 and the upper end 41a of the piston element 41 that protrudes from said tubular formation 50.

The two-part construction of the tubular formation 50 allows an angled lateral annular appendage 48a of the first membrane 48, formed near the lower end thereof, to be pressed. The interconnection between the parts of the tubular formation 50, meaning the crown 50b and the main portion 50a, which together attach the annular appendage 48a of the first membrane 48, can be a coupling by pressure, in the example by means of elastically deformable fasteners.

The seal between the parts that determine the expansion chamber 44 is ensured in the example by means of a second elastic membrane 49 in an annular form, the inner perimeter 49a of which is secured to the expanded base 43 of the piston element 41, the outer perimeter 49b of which is secured to the upper edge of the opening of the neck 32c of the container 3.

Other ways of ensuring the seal of the preloading 45 and expansion chamber 44 are possible.

Figure 3:
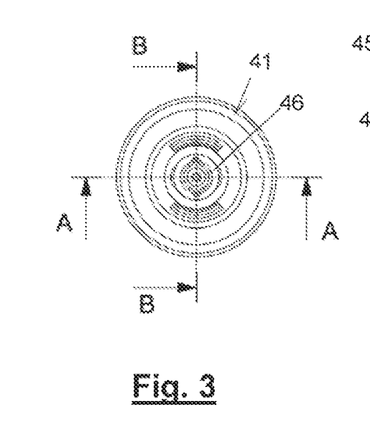
FIG. 3 is an upper perspective view of the piston element.
Figure 4A:
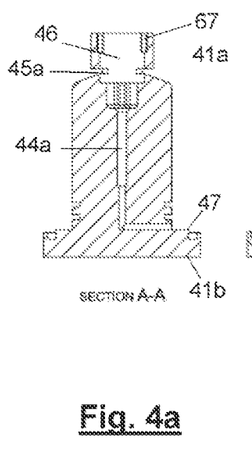
FIGS. 4a and 4b are cross-sectional views of the piston element according to the cutting planes AA and BB, respectively, of FIG. 3.
Figure 4B:
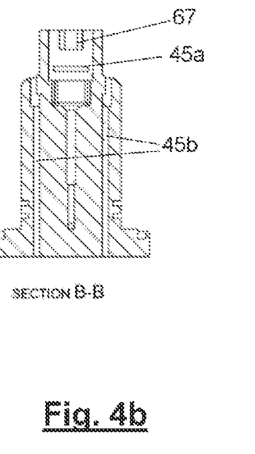
Figure 5:
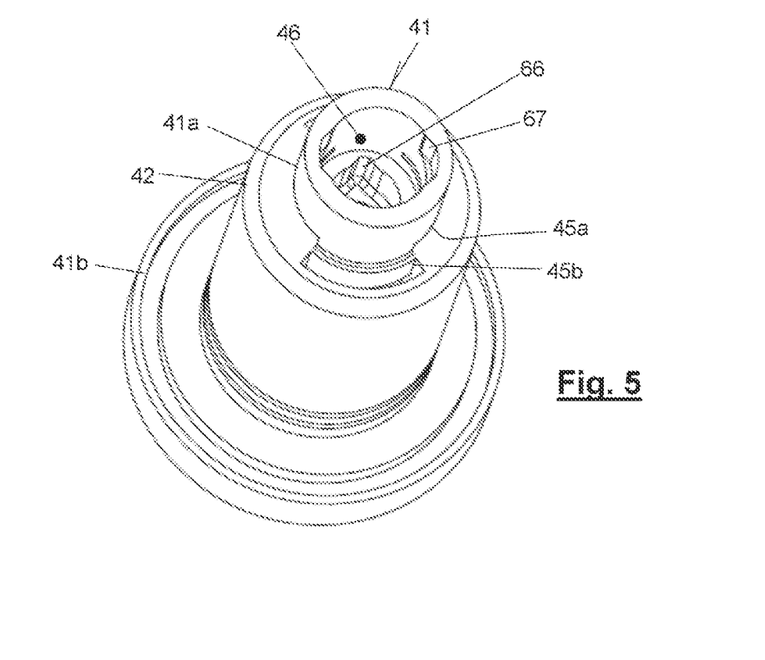
FIG. 5 is an upper perspective view of the piston element.

FIGS. 3 to 5 show a particular feature of the piston element 41 that plays an important role in the operation of the dispenser 4. Specifically, the figures show how the same comprises a first communication path 44a between the expansion chamber 44 and a collector 46 formed on the upper end of the piston element 41; a second communication path 45a between the preloading chamber 45 and the aforementioned collector 46 formed in the piston element 41; and a third communication path 45b between the inside of the container 3 and the preloading chamber 45.

Figure 7A:
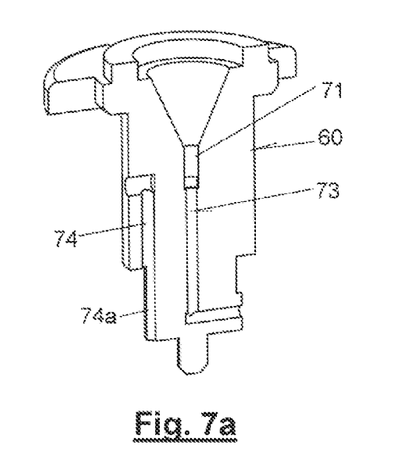
FIGS. 7a and 7b are longitudinal cross-sectional perspectives of the valve element according to the respective cutting planes at 90° to one another.
Figure 7B:
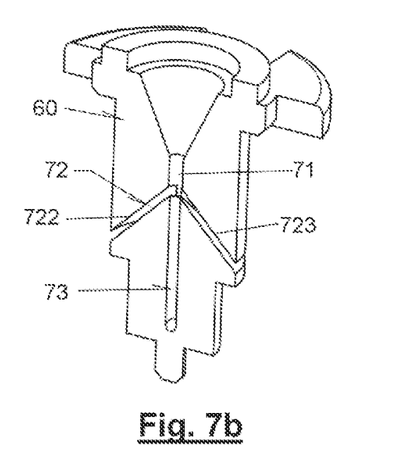

The collector 46 has a particular configuration, specially designed to receive the fit of a valve element 60 (see FIGS. 7A and 7b) with the capability to adopt different positions fitted in the collector 46. On the one hand, the valve element 60 can have axial movement with respect to the piston element 41 to enable or disable fluidic connections between the preloading chambers 45 and expansion chamber 44 with the outside; and the valve element 60 can also rotate about itself and adopt different angular positions with respect to the piston element 41. The features of this rotational capacity will be further explained below.

In the example, the first communication path 44a between the expansion chamber 44 and the collector 46 is formed by an angled conduit with a horizontal section (according to the orientation of the piston element represented in FIGS. 4A and 4b), in the direction of the fluid circulation, the inlet end of which flows into the expansion chamber 44, and a vertical section, the outlet end of which flows into the base of the collector 46.

In the example, the second communication path 45a between the preloading chamber 45 and the collector 46 is formed by two lateral grooves that pass through the wall of the upper end 41a of the piston element 41.

In the example, the third communication path 45b between the inside of the container 3 and the preloading chamber 45 is formed by two vertical conduits, the opposite ends of which flow into the container 3 and the preloading chamber 45, respectively.

In the dispenser 4, the valve element 60 is engaged with the trigger 62, which forms part of the actuation mechanism 6 of the dispenser 4, which in the example is formed by a hollow piece that covers the assembly formed by the tubular formation 50 and the upper end of the piston element 41. In the example, this hollow piece has a general bell shape and fits over the tubular formation 50 with the capability to rotate about itself, around the longitudinal axis of the device 1. The rotation of the trigger 62 will cause the rotation of the valve element 60, changing the angular position thereof with respect to the piston element 41.

The hollow piece that forms the trigger 62 also has the ability to move vertically, guided in its movement by the tubular formation 50.

The trigger 62 is held by elastic means (not visible in the drawings) that tend to arrange it in a constricted position against the annular edge 52 of the tubular formation 50.

As will be described in detail below, the trigger 62 and the valve element 60 are mutually related, so that a specific vertical movement of the trigger 62, in an upward direction, causes the movement of the valve element 60 by mechanical drag in order for them to move together in the upward direction.

The actuation mechanism 6 further comprises pumping means 61, able to pump and compress a volume of air captured from the outside to the expansion chamber 44.

In the example, the annular edge 52 of the tubular formation 50 has a vertical formation, like a perimeter skirt 52a, which determines along with the neck 32c of the container 3 an air suction chamber 54 by means of a check valve 53, such as a rubber retention duckbill check valve. This annular air suction chamber 54 is closed at the bottom by a piston member 63a of an actuator 63 that can be maneuvered by a user of the device 1. The actuator 63 is held by a spring 64 loaded between the annular edge 52 of the tubular formation 50 and the aforementioned piston member 63a.

The action of the spring 64 can be carried out by another component with elastic properties, separate or integral with either the actuator 63 or of the tubular formation 50.

Figure 13A:
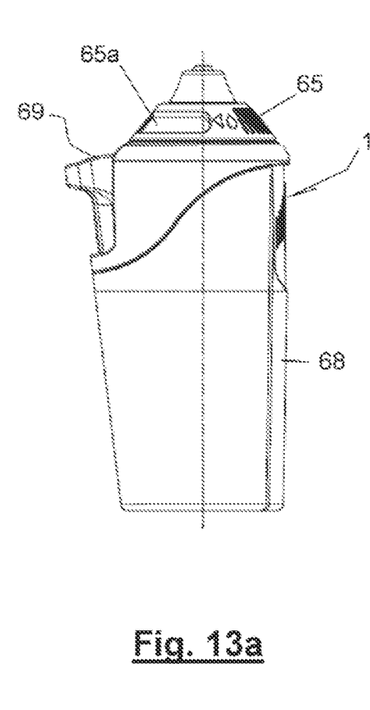
FIGS. 13a and 13b are views of the dispenser and ergonomic button.
Figure 13B:
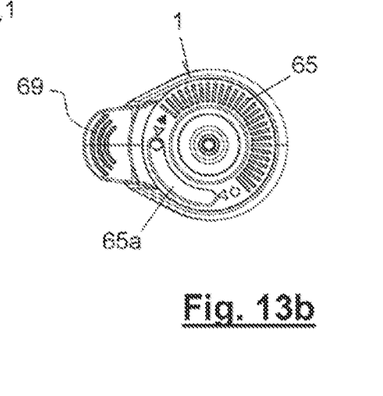

The dispenser 4 is completed by an outer selector 65, coupled in rotation with the trigger 62 but attached to an outer decorative element 68, which encases the container 3. FIGS. 13a and 13b show the impression of the assembly offered by the device 1 with this decorative element 68. In this example, the dispenser 1 is provided with an ergonomic button 69 associated with the actuator member 63 (hidden in FIGS. 13a and 13b).

The fastening of the selector 65 to the decorative element, for example by elastic fastening means, packages the components of the dispenser 4 in the default arrangement, shown in FIGS. 2a and 2b.

In this position, by default:
  The piston element 41 adopts a standby position B1, loaded by the pressure P of the pressurized substance 2 in the container 3, a position in which the annular step 42 of the piston element 41 is applied, with the interposition of the first membrane 48, against the crown 50b of the tubular formation 50.

In this position there is no floodable volume in the preloading chamber 45 and the expansion chamber 44 is contracted.

The valve element 60 adopts a closed position C1 with respect to the piston element 41. In this position there is no connection with the outside from the preloading chamber 45 or the expansion chamber 44, given that all of the connections between the collector 46 and the outside are blocked by the valve element 60.

The actuator 63 adopts a standby position A1, held by the spring 64.

If the user wants to dispense a dose of substance 2, starting with the position shown in FIGS. 2A and 2b, the user will actuate the actuator 63 in an upward direction. This will cause the release of a dose 2a of the substance 2 in two phases, as follows:

In a first phase of movement A1.1 the piston member 63a of the actuator 63 impels a volume of air 7 contained in the suction chamber 54 to the expansion chamber 44, the volume of the same expanding by pressure and, as a result, causing the movement of the piston element 41—downwards in the orientation of the drawings—until reaching a loading position B2, overcoming the force exerted by the substance 2 stored in the container 3 on this piston element.

This movement of the piston element 41 creates the necessary space in the preloading chamber 45 so that it automatically floods with the dose 2a of the substance 2 to be dispensed at a pressure p substantially equal to the pressure P that is inside the container 3, the substance 2 flowing from the container 3 to the preloading chamber 45 through the third communication path 45b with which the piston element 41 is provided.

Figure 6:
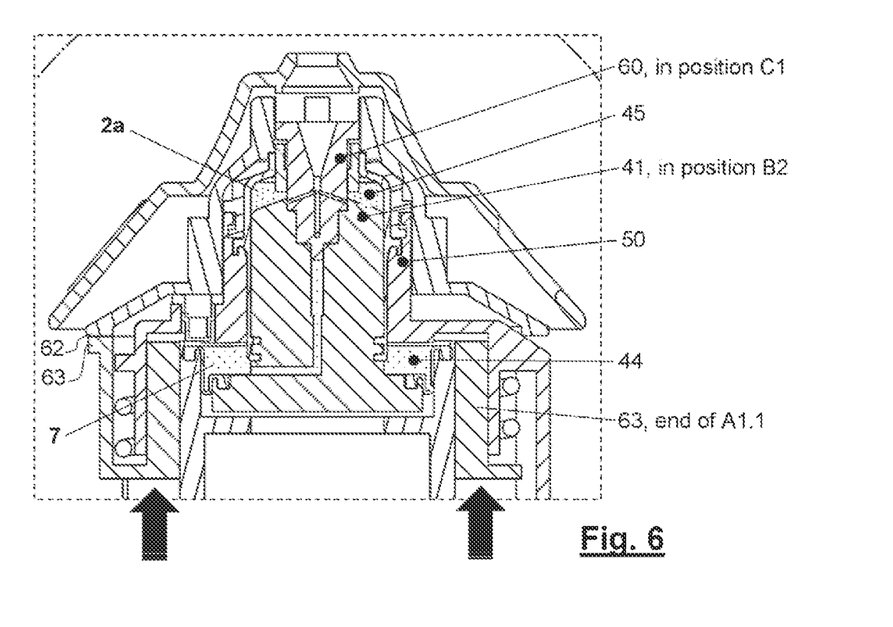
FIG. 6 is another detailed view of a longitudinal cross section of the device of FIG. 1, of the area corresponding to the dispenser, according to the same cutting plane as that of FIG. 2b, but now with the piston element adopting the loading position B2, the valve element continuing to adopt the closed position C1.

This state of the dispenser 4 is illustrated in FIG. 6.

Note that the valve element 60 moves with the piston element 41 by friction between the two, and continues to adopt the closed position C1 with respect to the piston element 41.

In a second movement phase A1.2, the actuator 63 makes contact with the trigger 62 and actuates it, moving it—upwards in the orientation of the drawings—dragging the valve element 60 in motion and arranging it in an ejection position C2, which enables the fluidic connection of the preloading chamber 45 and of the expansion chamber 44 with the outside. This connection allows the dose 2a of substance 2 accumulated in the preloading chamber 45, as well as the volume of air 7 accumulated in the expansion chamber used to move the piston element 41 in the first release phase, to be dispensed.

Figure 8:
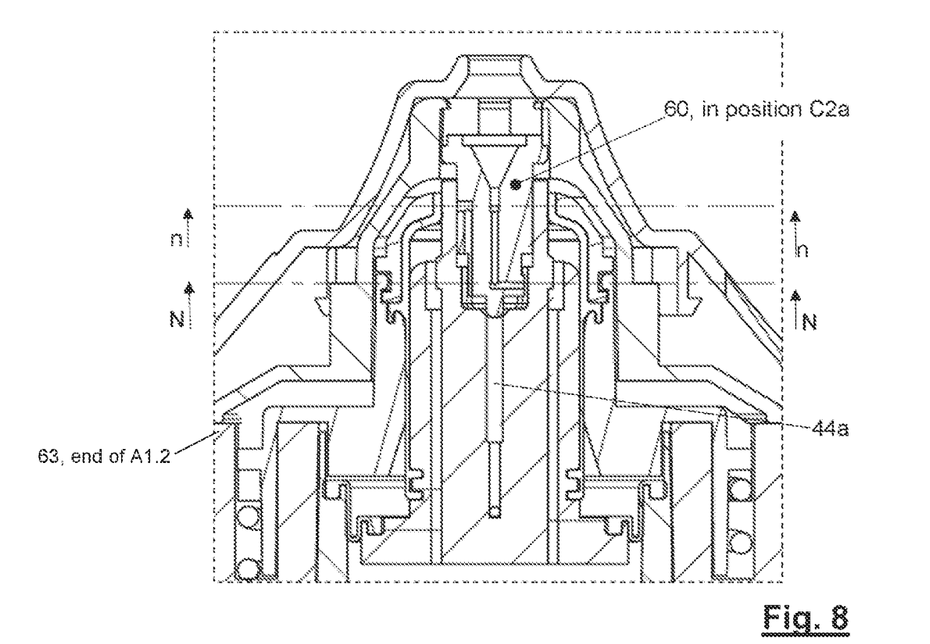
FIG. 8 shows the piston element adopting the loading position B2 and the valve element adopting a first ejection position C2a, suitable for dispensing a dose of the nebulized sub stance.
Figure 10:
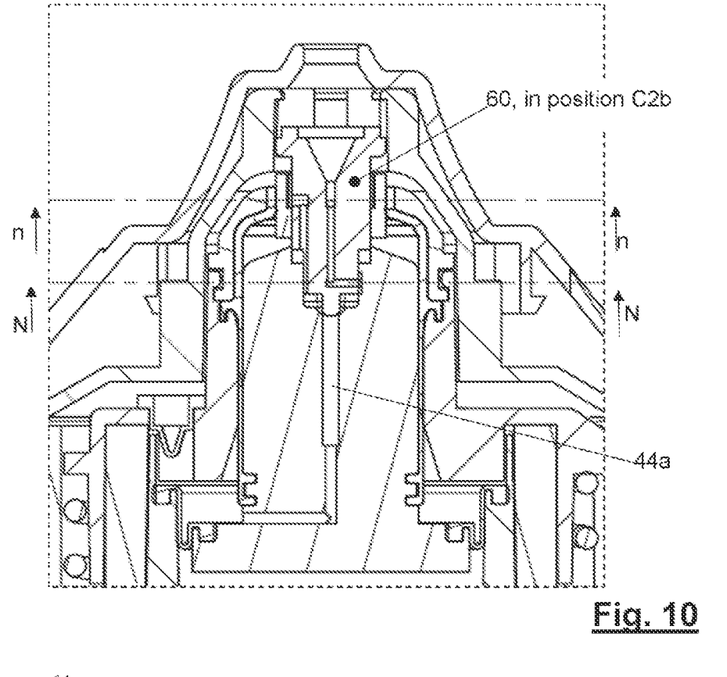
FIG. 10 shows the piston element adopting the loading position B2 and the valve element adopting a second ejection position C2b, suitable for dispensing a dose of the substance in the drop format.

FIGS. 8 and 10 show both the dispenser 4 at a moment immediately after the valve element 60 moves with respect to the piston element 41 from the closed position C1 to the ejection position C2, in each case the valve element 60 adopting a different angular position with respect to the piston element 41.

The evacuation of the expansion chamber 44 causes the piston element 41 to automatically go back to the standby position B1, due to the effect of the pressure P dose of the substance 2, closing the preloading chamber 45. By ceasing to exert an external force on the actuator 63, by the effect of the elastic means that act on the trigger 62 and by the effect of the spring 64 which acts on the same piston member 63a, the components of the dispenser 4 will go back to being arranged in the original position of FIGS. 2A and 2b.

The relationship between the valve element 60 and the piston element 41 in the device 1 that exemplifies the invention will be described in greater detail below.

In the aforementioned example, the valve element 60 (see FIGS. 7a and 7b) comprises a central ejection tube 71 and is prepared to produce an in-line mixture of the dose 2a of the substance to dispense (which comes from the preloading chamber 45) and of the volume of air 7 (which comes from the expansion chamber 44) in the same ejection tube 71, before the ejection thereof to the outside.

In fact, advantageously the volume of the preloading chamber 45 and the volume of air pumped to the expansion chamber 44 is selected in such a way that the proportions of the dose mass 2a and air mass 7 that are mixed cause an effervescent effect of the ejected substance 2, so as to achieve a nebulized dispensing.

To this end, the valve element 60 (see FIGS. 7a and 7b) has a distribution circuit for the dose 72 of the substance which makes it possible, in the ejection position C2, to channel the dose 2a supplied to the valve element 60 from different outlets to the central ejection tube 71 through the second communication path 45*a* of the piston element.

This distribution circuit for the dose 72 of the substance comprises two conduits 722, 723 which converge at the central ejection tube 71.

In turn, the valve element 60 has a first air distribution circuit 73 which, in the ejection position C2, makes it possible to channel to the central ejection tube 71 the volume of air 7 that reaches the collector 46 of the piston element 41 through the first communication path 44*a* of the latter to produce the in-line mixture dose of the substance 2 and this volume of air 7.

This first air distribution circuit 73 is formed in the example by an angled conduit with a horizontal section (according to the orientation of the valve element 60 represented in the drawings), in the direction of the circulation of the fluid, the inlet end of which flows into the collector 46 at a low level, and a vertical section axially aligned with the central ejection tube 71.

Notice that the conduits 722 and 723 that channel the dose 2*a* of the substance 2 converge at the same point of the central ejection tube 71 through which the volume of air 7 flows. In practice, this causes an air stream 7 to be injected into a peripheral current of the viscous substance 2, promoting the desired effervescent effect and the resulting nebulization of the mixture of substance and air.

The valve element 60 also has a second air distribution circuit 74 which, in the ejection position C2, makes it possible to channel to the outside, but outside of the central ejection tube 71, the air 7 that reaches the collector 46 through the first communication path 44*a*. This allows the dose 2*a* of substance 2 to be dispensed in drop format, without having been mixed with the volume of air 7 inside the dispenser 4.

This second air distribution circuit 74 is formed in the example by an angled conduit with a vertical section (according to the orientation of the valve element 60 represented in the drawings), in the direction of the circulation of the fluid, the inlet end of which flows into the collector 46 at a medium level, and a horizontal section that flows into the collector 46 at a high level. Associated with this conduit, the valve element 60 is provided with a vertical channel 74*a* that leaves a space with the wall of the collector 46 that is suitable for the flow of air 7 to the inlet opening of the conduit.

According to the angular position of the valve element 60 with respect to the piston element, the connection to the outside will be selectively enabled with one of said air distribution circuits 73 or 74, the connection to the outside always being enabled with the distribution circuit for the dose 72 of the substance.

To this end, the collector 46, in arrangement with the inlet openings of the first air distribution circuit 73 and outlet of the second air distribution circuit 74 of the valve element 60, is prepared to obstruct the passage of air through one of the same.

Specifically (see FIG. 5) at a low level the collector 46 only allows space for air to flow to the inlet opening of the first air distribution circuit 73 in a predetermined first angular window, by means of an entrance 66 formed on said collector 46 which, when coinciding with the inlet opening of the aforementioned first air distribution circuit 73, will allow a fluidic connection between the same and the collector 46. In this same circumstance, the outlet opening of the second air distribution circuit 74 will be closed by the wall of the collector 46 at the level of the aforementioned outlet.

Figures 9A, 9B:
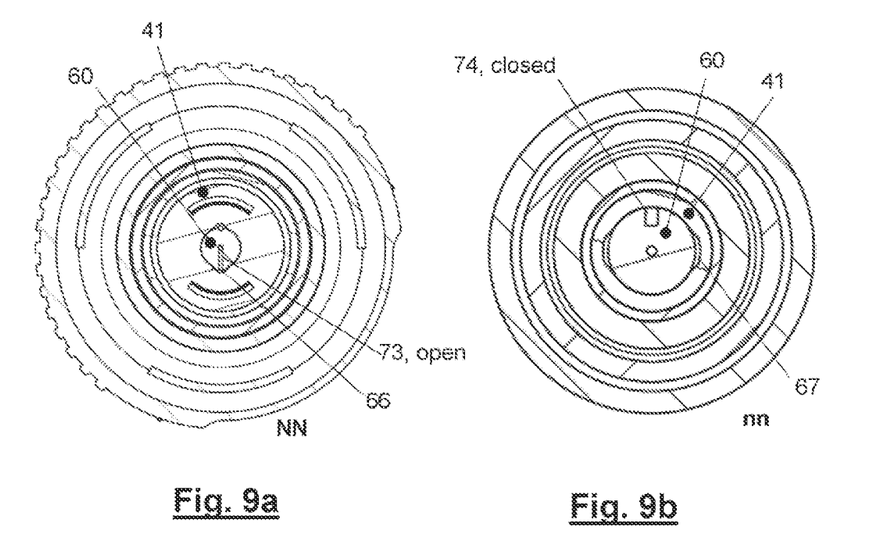
FIGS. 9a and 9b are transverse cross-sectional views in correspondence with the cutting planes NN and nn, indicated in FIG. 8.

This situation is represented in FIGS. 8, 9a and 9b, this first ejection position of the valve element 60 having been designated as C2*a*.

The collector 46 is suitable to operate differently in a second angular window that is different from the first one. Specifically, it is suitable for closing the inlet of the first air distribution circuit 73, given that the inlet opening thereof does not coincide with the aforementioned entrance 66, but leaving space for air to flow through the outlet opening of the second air distribution circuit 74 in this second angular window, by means of a notch or hollow 67 formed on said collector 46 at the level of the outlet opening of the second air distribution circuit 74, which will allow for a fluidic connection between this outlet opening and the outside, in the example outside of the valve element 60 and between the same and the upper crown 50b of the tubular formation 50.

Figures 11A, 11B:
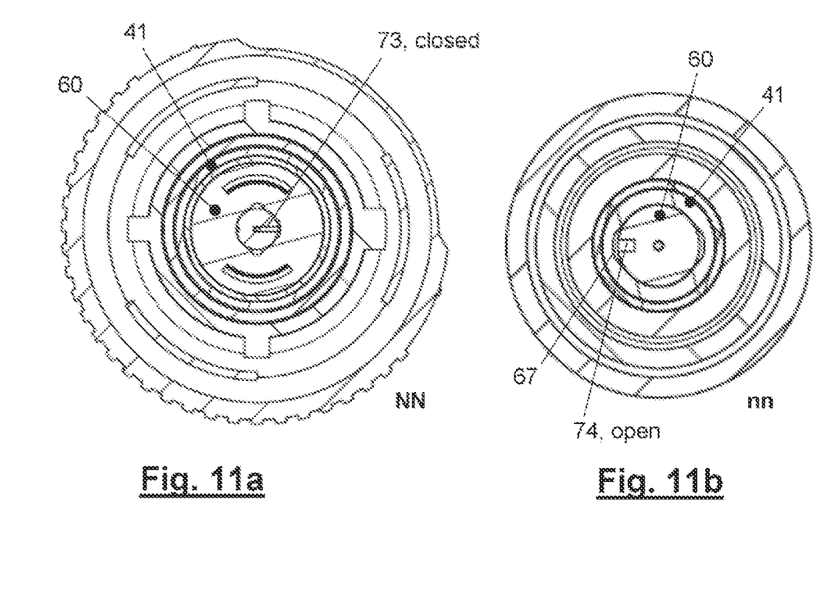
FIGS. 11a and 11b are transverse cross-sectional views in correspondence with the cutting planes NN and nn indicated in FIG. 10.

This situation is represented in FIGS. 10, 11a and 11b, this second ejection position of the valve element 60 having been designated as C2*b*.

In the embodiment that exemplifies the invention, between the first and second angular windows in an angle of approximately 90°.

Figure 1C:
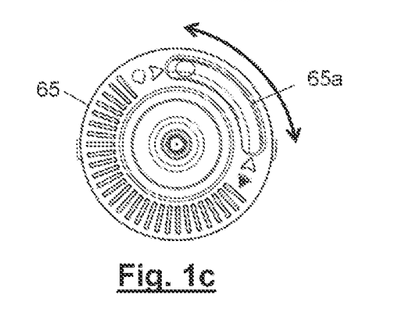
FIG. 1c, is a plan view of the device of FIG. 1.

In other words, to select the dispensing, nebulizing or drop mode, the user must rotate the outer decorative element 65 approximately 90°. As shown in the drawings (see FIG. 1c) the outer decorative element 65 has an engraving or another type of outer indication that is visually perceptible by the user, which indicates the current position of the valve element 60, and therefore whether the dispenser 4 is in the nebulizing mode or drop mode. In the example, the decorative element 65, which is coupled in rotation to the trigger 62 (in turn engaged with the valve element 60), has a groove 65a in a circumferential arc of 90° and through which a fixed rod passes or is inserted which acts as a rotational stop. The support of this rod on the opposite ends of the groove 65a will determine the positions corresponding to the nebulizer mode or drop mode.

Figure 12A:
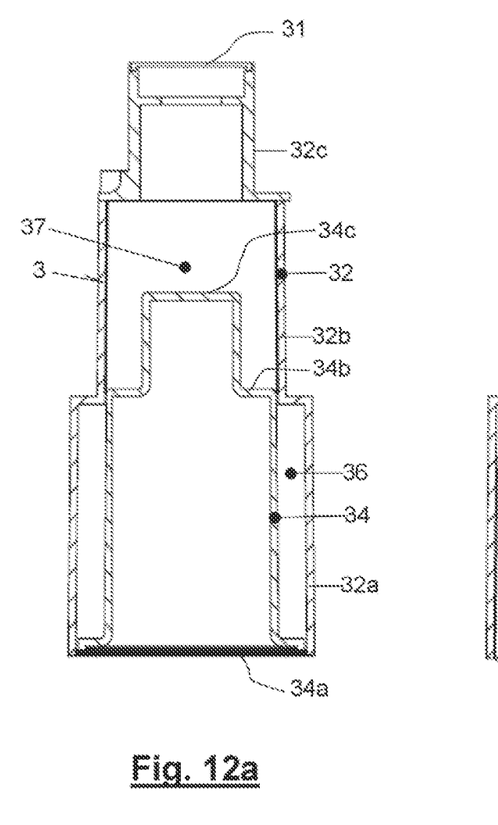
FIGS. 12a and 12b are detailed views of a longitudinal cross section of the container of the device of FIG. 1, when filled and emptied to the maximum, respectively.
Figure 12B:
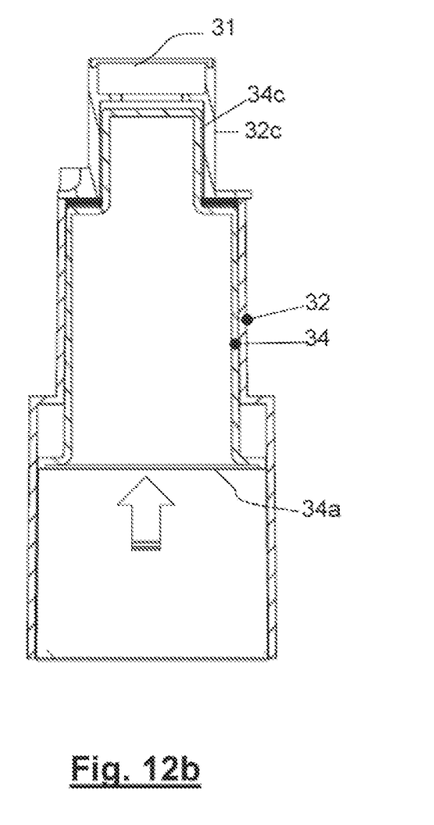

FIGS. 12a and 12b show that in the example the container 3 comprises an enclosure 32 made up of two pieces that together determine an end portion 32a, with a transverse cross section P1; a containment portion 32b, with a transverse cross section P2, wherein P1>P2; and an upper portion that provides the container with a neck 32c, securely coupled to the dispenser 4. In the example, the neck 32c is made up of a piece that is originally separated from the rest, although the invention contemplates other embodiments in which the enclosure 32 is a single piece.

A multiplier piston 34 and the enclosure 32 determine two chambers, a containment chamber 37 that contains the substance 2 and an annular chamber 36, subjected to vacuum conditions. Possible volumes for the containment chamber 37 are comprised between 10 ml and 20 ml, being 10 ml, for example.

To this end, the multiplier piston 34 is sealed to the inner wall of the outer enclosure 32 by means of membranes or mechanical seals.

When the containment chamber 37 is full of substance and the container 3 is closed by the dispenser 4, the containment chamber tends to collapse due to the effect exerted by the atmospheric pressure on the multiplier piston 34. This in turn exerts a pressure P on the substance that is greater than the atmospheric pressure due to the effect of the relationship between the surfaces of the multiplier piston 34 in contact with the outside and in contact with the substance 2.

One of the necessary conditions for the successful operation of this variant of the invention is that there be a good seal between the multiplier piston 34 and the enclosure 32. The seal can be a sliding contact with the help of joints, a grease or wax material, or alternatively by means of the use of elastic membranes, similar to the one used in the piston element 41 for sealing the preloading and expansion chambers 45 and 44, respectively, of the dispensing device 4.

In the example, the multiplier piston 34 is made of a rigid material and has an expanded head 34a, with a transverse cross section P1', corresponding to the transverse cross section P1 of the end portion 32a of the enclosure 32, and which slides with sealed support over the wall of said end portion; and a push-piston 34b, with a transverse cross section P2', corresponding to that of the transverse cross section P2 of the containment portion 32b of the enclosure 32, and which slides with sealed support over the wall of said containment portion, the push-piston 34b and the end portion 32a of the enclosure 32 determining the annular chamber 36 in under vacuum conditions, with a variable volume according to the position of the multiplier piston 34.

The P2/P1' ratio can be between 0.7 and 0.3, for example. An ideal relationship is that in which P2'/P1' is close to 0.5.

Possible values of P1' and P2' can be P1'=804 mm$^2$; and P2'=415 mm$^2$, for example.

The enclosure 32 has the neck portion 32c after the containment portion 32b, which has a reduced transverse cross section P3 and which serves as a coupling with the dispenser 4. Moreover, the multiplier piston 34 has a push-head 34c, with a transverse cross section P3' corresponding to that of the neck portion 32c of the enclosure 32 and which slides with sealed support over the wall of said neck portion 32c. This push-head 34c, matching with the neck 32c, allows the filling of the containment chamber 37 to be expedited.

The surface ratio P1'>P2' allows the storage of the substance 2a in the container 3 at an absolute pressure P approximately between 1.3 and 1.9 bar. This pressure will be kept constant regardless of the content of the remaining substance 2 in the container.

With regard to the pumping means 61 and corresponding to this pressure P range of the substance, the same are configured to accumulate air 7 from the outside in the expansion chamber 44 at an absolute pressure of approximately 1.9 bar, sufficient to overcome or at least equal the pressure P and move the piston element 41 from the standby position B1 thereof. Likewise, this air pressure 7, when mixed in-line with the dose 2a of the substance 2 to be dispensed, will be sufficient to cause the effervescent effect intended for nebulizing the mixture.

The invention claimed is:

1. A device suitable for dispensing a liquid substance, such as an ophthalmological substance, comprising
a container that contains at a pressure greater than atmospheric pressure the substance to be dispensed and
a dispenser for dispensing the substance to the outside that includes a piston element loaded by the pressure of the pressurized substance to adopt a standby position by default which prevents a preloading chamber from being flooded by a dose of the substance to be dispensed, and a valve element capable of enabling a connection between the aforementioned preloading chamber and the outside,
the device further incorporating
an actuation mechanism of the dispenser that sequentially first compresses a volume of air, the pressure of which is used for moving the piston element from its standby position allowing a dose of the substance to be able to flood the preloading chamber, to subsequently mechanically actuate the valve element to simultaneously enable the connection to the outside of the aforementioned preloading chamber, as well as of the volume of air previously used for moving the piston element from the standby position.

2. The device according to claim 1, characterized in that the actuation mechanism comprises
pumping means capable of pumping and compressing the volume of air captured from the outside, which is used to move the piston element from the standby position, and a trigger prepared to mechanically actuate the valve element, and in that
the actuation mechanism has a movable actuator, which in a single stroke of movement first actuates the pumping means causing the movement of the piston element from the standby position and causing the dose of the substance to flood the preloading chamber, and subsequently actuates the trigger, and with it the valve element to simultaneously enable the connection to the outside of the aforementioned preloading chamber as well as of the volume of air previously used for moving the piston element from the standby position.

3. The device according to claim 1, characterized in that the valve element is prepared to produce an in-line mixture of the dose of the substance and of the volume of air before the ejection of the in-line mixture to the outside.

4. The device according to claim 3, characterized in that the volume of the preloading chamber and the volume of pumped air is selected in such a way that the proportion of the dose mass and air mass that are mixed cause an effervescent effect of the ejected substance.

5. The device according to claim 2, characterized in that the dispenser comprises a tubular formation wherein the piston element is snugly movable between the standby position, which is the position normally adopted by the effect of the pressure exerted by the pressurized substance in the container on the aforementioned piston element, and a loading position, the piston element being related to one or several fixed parts of the device, such that it determines an expansion chamber, the increase in volume of which, by pumping air inside the same, promotes the movement of the piston element to the loading position, the piston element being related to another fixed part or parts of the device such that it determines the preloading chamber, floodable with the dose of the substance to be dispensed when the piston element moves to the loading position, the piston element further comprising a first communication path air between the expansion chamber and a collector formed in the piston element,
a second communication path for the dose of substance between the preloading chamber and the aforementioned collector formed in the piston element,
a third communication path for the substance between the inside of the container and the preloading chamber; in that
the valve element is plugged into the collector of the piston element with a degree of play and the relative position thereof with respect to the collector enables or disables fluidic connections from the first and second communication paths to the outside, the valve element being forced to adopt a closed position by default with respect to the piston element, which is the position that disables said fluidic connections to the outside; and in that
the actuator of the actuation mechanism is movable according to an actuation stroke from a standby position to a dispensing position, such that
in a first movement phase the actuator impels the air captured from the outside to the expansion chamber, compressing it in the same, increasing the volume thereof and promoting the movement of the piston element to the loading position, creating the necessary space in the preloading chamber so that through the third communication path is automatically flooded by the dose of substance to be ejected at a pressure substantially equal to the pressure inside the container, and
in a second movement phase the actuator drags the trigger in motion and with it the valve element, moving it with respect to the collector until the valve element adopts an ejection position which enables the aforementioned fluidic connections between the first and second communication paths of air and the dose of the substance, respectively, to the outside.

6. The device according to claim 5, characterized in that the valve element is plugged guided into the collector with play in an axial direction, coinciding with a direction of movement of the piston element between the standby and loading positions, the movement in this axial direction being the movement that enables or disables the fluidic connections between the first and second communication paths of air and of the dose of substance, respectively, to the outside.

7. The device according to claim 6, characterized in that the valve element comprises a central ejection tube and a distribution circuit for the dose of the substance which makes it possible in the ejection position to channel the dose supplied to the valve element from different outlets to the central ejection tube through the second communication path of the piston element.

8. The device according to claim 7, characterized in that the distribution circuit for the dose of the substance comprises at least two conduits which converge at the central ejection tube.

9. The device according to claim 7, characterized in that the valve element has a first air distribution circuit which, in a first ejection position, makes it possible to channel the air supplied to the valve element to the central ejection tube through the first communication path of the piston element to produce an in-line mixture of substance and air.

10. The device according to claim 7, characterized in that the valve element has a second air distribution circuit that makes it possible in a second ejection position to channel the air, supplied to the valve element through the first communication path, to the outside and via outside of the central ejection tube.

11. The device according to claim 9, characterized in that the valve element is plugged into the collector, an angular position between the valve element and the piston element being able to vary in order to select the air distribution circuit to be connected to the first communication path of the piston element that supplies the air to be ejected and thereby selecting whether or not it produces the mixture of substance and air.

12. The device according to claim 1, characterized in that the substance is enclosed in the container subjected to the pressure of a push-piston with an expanded head, to which atmospheric pressure is applied to one side and a vacuum to the other.

13. The device according to claim 12, characterized in that the container comprises an outer enclosure with a tubular configuration with at least an end portion, with a large transverse cross section, and a containment portion, with a small transverse cross section, originally full with the substance and in communication with the dispenser;

a multiplier piston with the expanded head, with a transverse cross section corresponding to that of the end portion of the outer enclosure and which slides with sealed support over a wall of said end portion, and the push-piston, with a transverse cross section corresponding to that of the containment portion of the outer enclosure and which slides with sealed support over a wall of said containment portion, the push-piston and the end portion of the enclosure determining an annular chamber under vacuum condition, with a variable volume according to the position of the multiplier piston.

14. The device according to claim 13, characterized in that the outer enclosure has a neck portion after the containment portion with a reduced transverse cross section and coupling to the dispenser; and in that the multiplier piston has a push-head, with a transverse cross section corresponding to that of the neck portion of the outer enclosure and which slides with support over a wall of said neck portion.

* * * * *